(12) United States Patent
Tsuji et al.

(10) Patent No.: US 7,317,107 B2
(45) Date of Patent: Jan. 8, 2008

(54) IMIDAZOLE 4-CARBOXAMIDE COMPOUNDS WITH ADENOSINE DEAMINASE INHIBITING ACTIVITY

(75) Inventors: Kiyoshi Tsuji, Osaka (JP); Tadashi Terasaka, Osaka (JP); Nobukiyo Konishi, Osaka (JP); Takeshi Kato, Osaka (JP); Katsuya Nakamura, Osaka (JP)

(73) Assignee: Astellas Pharma Inc., Tokyo (JP)

( * ) Notice: Subject to any disclaimer, the term of this patent is extended or adjusted under 35 U.S.C. 154(b) by 561 days.

(21) Appl. No.: 10/503,585

(22) PCT Filed: Feb. 12, 2003

(86) PCT No.: PCT/JP03/01459

§ 371 (c)(1),
(2), (4) Date: Aug. 12, 2004

(87) PCT Pub. No.: WO03/068768

PCT Pub. Date: Aug. 21, 2003

(65) Prior Publication Data

US 2005/0159462 A1 Jul. 21, 2005

(30) Foreign Application Priority Data

Feb. 15, 2002 (AU) ...................... PS0581

(51) Int. Cl.
| | | |
|---|---|---|
| C07D 417/00 | (2006.01) | |
| C07D 263/52 | (2006.01) | |
| C07D 277/66 | (2006.01) | |
| A61K 31/425 | (2006.01) | |
| A61K 31/42 | (2006.01) | |

(52) U.S. Cl. ...................... 548/400; 548/159; 548/217; 548/148; 514/367; 514/375

(58) Field of Classification Search ...................... None
See application file for complete search history.

(56) References Cited

U.S. PATENT DOCUMENTS

| | | | |
|---|---|---|---|
| 6,359,145 B1 | 3/2002 | Terasaka et al. | |
| 6,596,738 B1 | 7/2003 | Terasaka et al. | |
| 6,908,940 B2 * | 6/2005 | Tsuji et al. | 514/400 |
| 2004/0097571 A1 | 5/2004 | Tsuji et al. | |
| 2004/0236114 A1 * | 11/2004 | Terasaka et al. | 548/311.1 |

FOREIGN PATENT DOCUMENTS

| | | | |
|---|---|---|---|
| WO | 92 18483 | | 10/1992 |
| WO | 95 24395 | | 9/1995 |
| WO | 00 55155 | | 9/2000 |
| WO | WO 01/26605 | * | 4/2001 |
| WO | 01 53271 | | 7/2001 |

OTHER PUBLICATIONS

Patani et al., "Bioisosterism: A Rational Approach in Drug Design"; Chem. Rev. 1996, vol. 96, p. 3147-3176.*
www.acdlabs.com/iupac/nomenclature/79/r79_983.htm; "Heterocyclic Systems, Rule B-5. Radicals", 3 pages.*
http://cancer.about.com/od/leukemia/a/leukemiaprevent.htm, p. 1 of 1.*
http://en.wikipedia.org/wiki/Prodrug, 2 pages.*
Han et al., "Targeted Prodrug Design to Optimize Drug Delivery", AAPS PharmSci. 200, 2(1), article 6, DOI:10.1208/ps020106.*
http://en.wikipedia.org/wiki/Levodopa, 4 pages.*
http://en.wikipedia.org/wiki/Autoimmune_disease, 6 pages.*
http://bccc.pair.com/autoimmu.htm, 3 pages.*
http://www.nlm.nih.gov/medlineplus/ency/article/000816.htm.*
Kuno et al., "Anti-inflammatory activity of non-nucleosie adenosine deaminase inhibitor FR234938", European Journal of Pharmacology, 534 (2006), 241-249.*
Barnes, P.J. "Mediators of Chronic Obstructive Pulmonary Disease", Pharmacol. Rev. 56 (2004), 515-548.*
Kay, A.B. "Allergy and Allergic Diseases, First of Two Parts", N. Engl J Med, vol. 344, p. 30-37.*
McCulloch et al. "Signalling Platforms that modulate the inflammatory response: new targets for drug development", Nature Reviews/Drug Discovery, vol. 5 (2006), 864-876.*
http//www.mayoclinic.com/health/periodontitis/DS00369/DSECTION=7, 2 pages.*
Singh et al. "Differential Expression of Inflammatory Cytokines and Chemokines Genes by Homocystein in the Human Retinal Pigmented Epithelial Cells", FASEB, 2006, 20, A719 (abstract).*
http://www.emedicinehealth.com/leukemia/page12_em.htm, 2 pages.*

(Continued)

*Primary Examiner*—Rebecca Anderson
*Assistant Examiner*—Sun Jae Y Loewe
(74) *Attorney, Agent, or Firm*—Oblon, Spivak, McClelland, Maier & Neustadt, P.C.

(57) ABSTRACT

Imidazole compounds having adenosine deaminase inhibitory activity represented by the formula (I): wherein $R^1$ is optionally substituted aryl or optionally substituted heteroaryl, $R^2$ is lower alkyl; $R^3$ is hydroxy or protected hydroxy; X is O or S; and -A- is lower alkylene, its prodrug, or their salt. The compounds are useful for treating and/or preventing diseases for which adenosine is effective

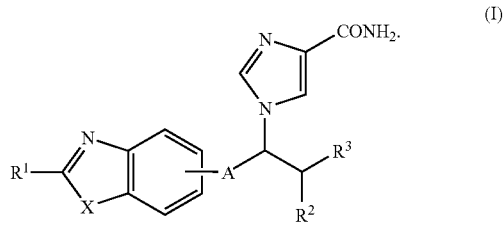

27 Claims, No Drawings

OTHER PUBLICATIONS

Terasaka et al. "Structure-Based Design and Synthesis of Non-Nucleoside, Potent, and Orally Bioavailable Adenosine Deaminase Inhibitors", J. Med. Chem. 2004, 47, 2728-2731.*

Grever et al. "Pentostatin in the treatment of hairy cell leukemia", Best Practice & Research Clinical Haematology, vol. 16, p.191-99.*

Cristalli, Gloria et al. "Adenosine Deaminase Inhibitors: Synthesis and Structure- Activity Relationships of Imidazole Analogues of erythro-9-(2-Hydroxy-3-nonyl)adenine". Journal of Medicinal Chemistry, vol. 34, No. 3, pp. 1187-1192, XP002119563, ISSN: 0022-2623 1991.

* cited by examiner

IMIDAZOLE 4-CARBOXAMIDE COMPOUNDS WITH ADENOSINE DEAMINASE INHIBITING ACTIVITY

TECHNICAL FIELD

This invention relates to novel imidazole compounds having pharmacological activity, to a process for their production and to a pharmaceutical composition containing the same.

BACKGROUND ART

Adenosine (Ado) is an endogenous purine nucleoside released by cells as part of the normal metabolic machinery. Ado has wide variety of biological activities, namely potent antiinflammatory and immunosuppressive properties, protective effects in cardiovascular and cerebrovascular ischemia, anticonvulsant effects and modulation effects of platelet aggregation, lipolysis, glycogenesis, blood flow and neurotransmission. Ado shows the biological activities by binding to its receptors anchored in the cell membrane. Therefore, it is the beneficial treatment for many diseases to perform the pharmacological elevation of extracellular Ado concentrations.

Adenosine deaminase (ADA) catalyzes an essentially irreversible deamination of adenosine or deoxyadenosine to inosine or deoxyinosine, respectively. In the last 10 years, ADA, which was considered to be cytosolic, has been found on the cell surface of many cells. Thus, blocking ADA activity with specific inhibitor is the potent way to elevate Ado concentrations in biological systems and the beneficial treatment for many diseases.

Some compounds have been known to have inhibitory activity of ADA (J. Med. Chem. 27, 274-278, 1984; ibid. 31, 390-393, 1988; ibid. 34, 1187-1192, 1991; ibid. 35, 4180-4184, 1992; ibid. 37, 305-308, 1994; ibid. 37, 3844-3849, 1994; and WO98/02166).

Known imidazole compounds with pharmaceutical activity other than ADA inhibitory activity are described in U.S. Pat. No. 4,451,478 and WO97/26883.

Furthermore, some imidazole derivatives having ADA inhibitory activity have been reported, for example, as described in Drug Development Research 28, 253-258, 1993.

DISCLOSURE OF THE INVENTION

This invention relates to novel imidazole compounds, which have pharmaceutical activity such as ADA inhibiting activity, to a process for their production, to a pharmaceutical composition containing the same and to a use thereof.

One object of this invention is to provide the novel imidazole compounds, which have an ADA inhibiting activity.

Another object of this invention is to provide a process for production of the imidazole compounds.

A further object of this invention is to provide a pharmaceutical composition containing the imidazole compound as an active ingredient.

Still further object of this invention is to provide a use of the imidazole compound for manufacturing a medicament for treating or preventing various diseases, or a method of treating or preventing various diseases by administering the imidazole compound in an effective amount to elevate adenosine concentration.

The imidazole compound of this invention can be represented by the following formula (I):

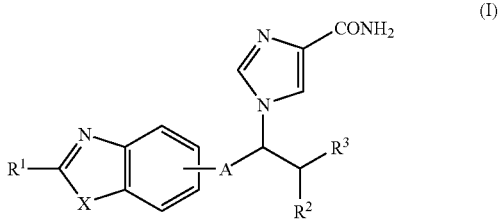

wherein $R^1$ is optionally substituted aryl or optionally substituted heteroaryl, $R^2$ is lower alkyl;

$R^3$ is hydroxy or protected hydroxy;

X is O or S; and

-A- is lower alkylene, its prodrug, or their salt.

In the compound of formula (I), $R^1$ is preferably thienyl, benzothiophenyl, or aryl optionally substituted with substituent(s) selected from the group consisting of halogen, lower alkyl, lower alkoxy, lower alkylthio, lower alkylsulfinyl and lower alkylsulfonyl. $R^2$ is preferably methyl. -A- is preferably ethylene.

Preferable Examples of compounds within this invention are:

(1) 1-{(3R,4S)-4-Hydroxy-1-[2-(4-chlorophenyl)-4-benzoxazolyl]-3-pentyl}-imidazole-4-carboxamide hydrochloride (E0017), (2) 1-[(3R,4S)-4-Hydroxy-1-(2-phenyl-4-benzoxazolyl)-3-pentyl]-imidazole-4-carboxamide (E0018), (3) 1-{(3R,4S)-4-Hydroxy-1-[2-(4-methoxyphenyl)4-benzoxazolyl]-3-pentyl}-imidazole-4-carboxamide hydrochloride (E0020), (4) 1-{(3R,4S)-4-Hydroxy-1-[2-(4-ethoxyphenyl)-4-benzoxazolyl]-3-pentyl}-imidazole-4-carboxamide hydrochloride (E0023), (5) 1-{(3R,4S)-4-Hydroxy-1-[2-(4-chlorophenyl)-7-benzoxazolyl]-3-pentyl}-imidazole-4-carboxamide (E0024), (6) 1-{(3R,4S)-4-Hydroxy-1-[2-(4-methoxyphenyl)-7-benzoxazolyl]-3-pentyl}-imidazole-4-carboxamide hydrochloride (E0025), (7) 1-{(3R,4S)-4-Hydroxy-1-[2-(4-methylthiophenyl)-7-benzoxazolyl]-3-pentyl}-imidazole-4-carboxamide (E0026), (8) 1-{(3R,4S)-4-Hydroxy-1-[2-(4-methylphenyl)-7-benzoxazolyl]-3-pentyl}-imidazole-4-carboxamide (E0027), (9) 1-{(3R,4S)-4-Hydroxy-1-[2-(2-thienyl)-7-benzoxazolyl]-3-pentyl}-imidazole-4-carboxamide hydrochloride (E0028),

(10) 1-{(3R,4S)-4-Hydroxy-1-[2-(2-benzothiophenyl)-7-benzoxazolyl]-3-pentyl}-imidazole-4-carboxamide hydrochloride (E0029),

(11) 1-{(3R,4S)-4-Hydroxy-1-[2-(3-chlorophenyl)-4-benzoxazolyl]-3-pentyl}-imidazole-4-carboxamide hydrochloride (E0030),

(12) 1-{(3R,4S)-4-Hydroxy-1-[2-(4-propoxyphenyl)-4-benzoxazolyl]-3-pentyl}-imidazole-4-carboxamide hydrochloride (E0031), and

(13) 1-{(3R,4S)-4-Hydroxy-1-[2-(4-chlorophenyl)-5-benzoxazolyl]-3-pentyl}-imidazole-4-carboxamide hydrochloride (E0032).

The compound (I), its prodrug, or their salt can be prepared by the following processes. In the following formulae, compounds may be prodrugs or their salts.

Process 1

The compound (I) wherein $R^3$ is not hydroxy can be obtained by reacting a compound of formula (III):

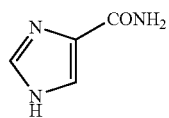

(III)

with a compound of formula (IV):

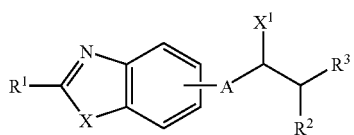

(IV)

wherein $R^1$, $R^2$, $R^3$, X and A are as defined above, and $X^1$ is hydroxy or a leaving group (such as halogen, alkanesulfonyloxy, arylsulfonyloxy, and the like), provided that $R^3$ is not hydroxy;

In this process the compound (I) can be produced by reacting the compound (IV), where $X^1$ is hydroxy, with alkanesulfonyl chloride (e.g. methanesulfonyl chloride, etc.) or arylsulfonyl chloride (e.g. toluenesulfonyl chloride, etc.) in the presence of a base such as triethylamine or pyridine in a solvent, which does not adversely affect the reaction, such as dichloromethane, chloroform, tetrahydrofuran, or diethyl ether from 0° C. to room temperature for about 1 hour and reacting the resulting sulfonate with the compound (III) in the presence of a base such as sodium hydride, potassium tert-butoxide, or potassium carbonate in a solvent such as dimethylformamide (DMF) from room temperature to 100° C. Alternatively, the compound (II) can be reacted with the compound (IV) in the presence of a base such as sodium methoxide, potassium tert-butoxide, or sodium hydride to give the compound (I).

Process 2

The compound (I) wherein $R^3$ is hydroxy can be obtained by reacting a compound of formula (I-1):

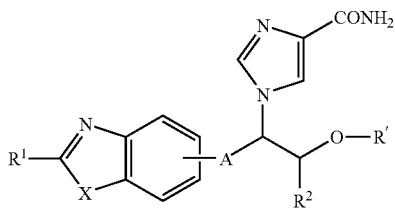

(I-1)

wherein $R^1$, $R^2$, X and A are as defined above, and R' is hydroxy protective group, with a deprotecting agent.

The compound (I-1) can be reacted with a deprotecting agent such as palladium hydroxide on carbon/cyclohexane, iodotrimethylsilane or tetrabutylammonium fluoride in a solvent, which does not adversely affect the reaction, such as ethanol, chloroform or tetrahydrofuran. The reaction temperature is not critical and the reaction is usually carried out under cooling to warming.

In the following, suitable examples of the definitions to be included within the scope of the invention are explained in detail.

The term "lower" means a group having 1 to 6 carbon atom(s), unless otherwise provided.

Suitable "lower alkyl" and lower alkyl moiety of "lower alkoxy", "lower alkylthio", "lower alkylsulfinyl", "lower alkylsulfonyl" and "lower alkylamino" include a straight or branched one such as methyl, ethyl, propyl, isopropyl, butyl, isobutyl, tert-butyl, pentyl, hexyl, or the like, with methyl being preferred.

Suitable "lower alkylene" may be straight or branched one having 1 to 8 carbon atom(s), such as methylene, ethylene, trimethylene, tetramethylene, pentamethylene, hexamethylene, or the like, with ethylene being preferred.

Suitable "halogen" means fluorine, chlorine, bromine, or iodine.

Suitable "aryl" include phenyl, naphthyl, or the like, with phenyl being preferred.

The term "optionally substituted aryl" means aryl which is optionally substituted with one or more substituent(s) selected from halogen, lower alkyl, lower alkoxy, lower alkylthio, lower alkylsulfinyl and lower alkylsulfonyl, and the like. Examples of the "optionally substituted aryl" include unsubstituted aryl such as phenyl, naphthyl, or the like; haloaryl such as 3-fluorophenyl, 4-fluorophenyl, 3-chlorophenyl, 4-chlorophenyl, 2,3-dichlorophenyl, 3,4-dichlorophenyl, 3-bromophenyl, 4-bromophenyl, 3,5-dibromophenyl, 4-bromo-2-fluorophenyl, 6-chloro-1-naphthyl, 7-chloro-1-naphthyl, or the like; lower alkylaryl such as 4-methylphenyl, 4-isopropylphenyl, 3,5-dimethylphenyl, or the like; halo(lower)alkylaryl such as 3,5-bis(trifluoromethyl)phenyl or the like; lower cycloalkylaryl such as 4-cyclohexylphenyl or the like; lower alkoxyaryl such as 4-methoxyphenyl, 3,5-dimethoxyphenyl, 4-ethoxyphenyl, 4-propoxyphenyl, or the like; lower alkylthioaryl such as 2-(methylthio)phenyl, 4-(methylthio)phenyl, or the like; aryl substituted with heterocyclicthio which may be substituted with halogen, such as 4-(2-thienylthio)phenyl, 4-(5-chloro-2-thienylthio)phenyl, or the like; arylaryl such as 4-biphenylyl or the like; aryl(lower)alkylaryl such as 4-(1-methyl-1-phenylethyl)phenyl or the like; aryloxy(lower)alkylaryl such as 3-(phenoxymethyl)phenyl or the like; aryl(lower)alkenylaryl such as 4-styrylphenyl or the like; arylthioaryl such as 4-(phenylthio)phenyl or the like; aryl substituted with aryloxy which may be substituted with halogen, such as phenoxyphenyl, 4-fluorophenoxyphenyl, or the like; aryl substituted with heterocyclic group which may be substituted with cyano, such as 4-(2-thienyl)phenyl, 4-(2-pyridyl)phenyl, 4-(1,2,3-thiadiazol-4-yl)phenyl, 4-(2-cyano-1-pyrrolyl)phenyl, or the like; and cyanoaryl such as 4-cyanophenyl or the like.

Suitable "heteroaryl" in the term "optionally substituted heteroaryl" means saturated or unsaturated, heteromonocyclic or condensed heterocyclic rings having preferably 1 to 3, in particular 1 to 2, identical or different heteroatom(s), to which it is possible to fuse a benzene ring. Heteroatom(s) in the heteroaryl are oxygen, sulfur and nitrogen, and the like. Examples which may be mentioned are following:

a) Unsaturated 3- to 8-membered, preferably 5- or 6-membered, heteromonocyclic group such as pyrrolyl, pyrrolinyl, pyridyl, pyrazolyl, imidazolyl, pyrimidyl, pyrazinyl, pyridazinyl, diazepinyl (e.g. 1,4-diazepinyl, etc.), triazolyl (e.g. 4H-1,2,4-triazolyl, 1H-1,2,3-triazolyl, 2H-1,2,3-triazolyl, etc.), triazynyl (e.g. 1,3,5-triazynyl, 1,2,4-triazynyl, 1,2,3-triazynyl, etc.), dihydrotriazinyl (e.g. 4,5-dihydro-1,2,4-triazinyl, 2,5-dihydro-1,2,4-triazinyl, etc.), furyl, pyranyl, oxepinyl, dioxolyl, thienyl, thiepinyl, oxazolyl, isoxazolyl, oxadiazolyl (e.g. 1,2,4-oxadiazolyl, 1,3,4-oxadiazolyl, 1,2,5-oxadiazolyl, etc.), oxazinyl (e.g. 1,3-oxazinyl, 1,4-oxazinyl, etc.), thiazolyl, 1,2-thiazolyl, thiazolinyl, thiadiazolyl (e.g. 1,2,4-thiadiazolyl, 1,3,4-thiadiazolyl, 1,2,5-thiadiazolyl, 1,2,3-thiadiazolyl, etc.), and the like;

b) Unsaturated condensed (preferably bicyclic) 7- to 13-membered, preferably 9- or 10-membered, heterocyclic group such as indolyl, isoindolyl, indolinyl, indolizinyl, quinolyl, isoquinolyl, benzimidazolyl, indazolyl, benzotriazolyl, carbazolyl, quinoxalinyl, imidazopyridyl (e.g. imidazo[4,5-c]pyridyl, etc.), phthalazinyl, naphthyridinyl, quinazolinyl, cinnolinyl, benzofuryl, isobenzofuryl, benzodioxolyl, benzothienyl, benzoxazolyl, benzoxadiazolyl, benzothiazolyl, benzothiadiazolyl, imidazothiazolyl, benzisothiazolyl, and the like;

c) Saturated 3- to 8-membered, preferably 5- or 6-membered, heterocyclic group such as azetidinyl, pyrrolidinyl, imidazolidinyl, piperidinyl, piperidino, pyrazolidinyl, piperazinyl, oxolanyl, dioxolanyl, tetrahydropyranyl, dioxacyclohexyl, 1,4-dioxanyl, tetrahydrothienyl, morpholinyl, morpholino, oxazolidinyl (e.g. 1,3-oxazolidinyl etc.), thiazolidinyl, isothiazolidinyl, and the like; or the like, preferably thienyl and benzothienyl.

The term "optionally substituted heteroaryl" means above-mentioned "heteroaryl" which is optionally substituted with one or more substituent(s) selected from halogen, lower alkyl, lower alkoxy, lower alkylthio, lower alkylsulfinyl and lower alkylsulfonyl, oxo, sulfo, hydroxy, optionally substituted aryl, and the like; in case that the "heteroaryl" has plural substituents, they may be the same or different each other, but, needless to say, "heteroaryl" may not have substituent.

Suitable "protected hydroxy" includes lower alkoxy optionally substituted with aryl; acyloxy; or tri(lower)alkylsilyloxy (i.e., trimethylsilyloxy, tert-butyldimethylsilyloxy, etc.); or the like.

Suitable hydroxy protective groups in the protected hydroxy group include lower alkyl optionally substituted with aryl; acyl; tri(lower)alkylsilyl (i.e., trimethylsilyl, tert-butyldimethylsilyl, etc.); or the like. Here, suitable "acyl" includes acetyl, trifluoroacetyl, or the like.

Suitable "leaving group" includes halogen, acyloxy (e.g. acetyloxy, trifluoroacetyloxy, etc.), lower alkylsulfonyloxy (e.g. methanesulfonyloxy, etc.), triarylphosphinoxy (e.g. —O—P$^+$(C$_6$H$_5$)$_3$, etc.), or the like.

Suitable salts of the compounds of the present invention are pharmaceutically acceptable conventional non-toxic salts and can be an organic acid addition salt (e.g. formate, acetate, trifluoroacetate, maleate, tartarate, oxalate, methanesulfonate, benzenesulfonate, toluenesulfonate, etc.), an inorganic acid addition salt (e.g. hydrochloride, hydrobromide, sulfate, phosphate, etc.), a salt with an amino acid (e.g. aspartic acid salt, glutamic acid salt, etc.), or the like.

The "prodrug" means the derivatives of compounds of the present invention having a chemically or metabolically degradable group, which becomes pharmaceutically active after biotransformation.

The compounds of formula (I) may contain one or more asymmetric centers and thus they can exist as enantiomers or diastereoisomers. Furthermore certain compounds of formula (I) which contain alkenyl groups may exist as cis- or trans-isomers. In each instance, the invention includes both mixtures and separate individual isomers.

The compounds of the formula (I) may also exist in tautomeric forms and the invention includes both mixtures and separate individual tautomers.

The compound of the formula (I) and its salt can be in a form of a solvate, which is included within the scope of the present invention. The solvate preferably include a hydrate and an ethanolate.

Also included in the scope of invention are radiolabelled derivatives of compounds of formula (I) which are suitable for biological studies.

The compound of the present invention can be purified by any conventional purification methods employed for purifying organic compounds, such as recrystallization, column chromatography, thin-layer chromatography, high-performance liquid chromatography and the like. The compounds can be identified by conventional methods such as NMR spectrography, mass spectrography, IR spectrography, elemental analysis, and measurement of melting point.

The compound (I), its prodrug, or their salt can be administered alone or in the form of a mixture, preferably, with a pharmaceutical vehicle or carrier.

The active ingredient of this invention can be used in the form of a pharmaceutical preparation, for example, in solid, semisolid or liquid form, which contains a compound (I), as an active ingredient, in admixture with an organic or inorganic carrier or excipient suitable for oral, external (topical), enteral, intravenous, intramuscular, parenteral or intramucous applications. The active ingredient can be formulated, for example, with the conventional non-toxic, pharmaceutically acceptable carriers for ointment, cream, plaster, tablets, pellets, capsules, suppositories, solution (saline, for example), emulsion, suspension (olive oil, for example), aerosols, pills, powders, syrups, injections, troches, cataplasms, aromatic waters, lotions, buccal tablets, sublingual tablets, nasal drops and any other form suitable for use. The carriers which can be used are water, wax, glucose, lactose, gum acacia, gelatin, mannitol, starch paste, magnesium trisilicate, talc, corn starch, keratin, paraffin, colloidal silica, potato starch, urea and other carriers suitable for use in manufacturing preparations, in solid, semisolid, or liquid form, and in addition auxiliary, stabilizing, thickening and coloring agents and perfumes may be used. The active compound is included in a pharmaceutical composition in an effective amount sufficient to produce the desired effect upon the process or condition of the diseases.

The active ingredient can be formulated into, for example, preparations for oral application, preparations for injection, preparations for external application, preparations for inhalation, preparations for application to mucous membranes.

Mammals which may be treated by the present invention include livestock mammals such as cows, horses, etc., domestic animals such as dogs, cats, rats, etc. and humans, preferably humans.

While the dosage of therapeutically effective amount of the compound (I) will vary depending upon the age and condition of each individual patient, an average single dose to a human patient of about 0.01 mg, 0.1 mg, 1 mg, 10 mg, 50 mg, 100 mg, 250 mg, 500 mg, and 1000 mg of the compound (I) may be effective for treating the above-mentioned diseases. In general, amounts between 0.01 mg/body and about 1,000 mg/body may be administered per day.

An ADA inhibitor, such as the compound (I) or its pharmaceutically acceptable salts of this invention, possesses ADA inhibiting activity and are thus useful in immunomodulation, especially immunosuppression, antiinflammation and treatment and prevention of various diseases for which Ado is effective. Examples of the diseases are as follows:
a) Autoimmune diseases and inflammatory conditions, e.g. various pains collagen diseases, autoimmune diseases, various immunity diseases, and the like in human beings or animals, and more particularly for the treating and/or preventing inflammation and pain in joint and muscle (e.g. osteoarthritis, gouty arthritis, etc.), inflammatory skin condition (e.g. sunburn, eczema, etc.), inflammatory eye condition (e.g. conjunctivitis, etc.), lung disorder in which inflammation is involved (e.g. asthma, bronchitis, pigeon fancier's disease, farmer's lung, etc.), condition of the gastrointestinal tract associated with inflammation (e.g. aphthous ulcer, Crohn's disease, atrophic gastritis, ulcerative colitis, celiac disease, regional ileitis, irritable bowel syndrome, etc.), periodontitis or gingivitis, (inflammation, pain and tumescence after operation or injury), pyrexia, pain and other conditions associated with inflammation, systemic lupus erythematosus, scleroderma, polymyositis, polychondritis, periarteritis nodosa, ankylosing spondylitis, inflammatory chronic renal condition (e.g. nephrotic syndrome, glomerulonephritis, membranous nephritis, etc.), acute nephritis, rheumatic fever, Sjogren's syndrome, Behcet disease, thyroiditis, type 1 diabetes, dermatomyositis, chronic active hepatitis, acute hepatitis, myasthenia gravis, idiopathic sprue, Grave's disease, multiple sclerosis, primary billiary cirrhoris, Reiter's syndrome, autoimmune hematological disorders (e.g. hemolytic anemia, pure red cell anemia, idiopathic thrombocytopenia, aplastic anemia, etc.), uveitis, contact dermatitis, psoriasis, Kawasaki disease, sarcoidosis, Wegner's granulomatosis, Hodgkin's disease, or the like;
b) Organ or tissue allo- or xeno-transplant rejection, e.g. kidney, liver, heart, lung, combined heart-lung, bone marrow, islet cells, pancreatic, skin, chromaffin or dopamine producing cells, small bowel, or corneal transplantation. Treating and/or preventing graft-versus-host disease, such as occurs following bone marrow transplantation;
c) Chronic pain (e.g. cancer pain, diabetic neuropathy, etc);
d) Various leukemias, including virus induced, or various induced lymphomas;
e) Various rheumatisms, such as articular rheumatism, chronic rheumatism, lumbar rheumatism, inflammatory rheumatism, muscular rheumatism, or virus induced rheumatism, or the like;
f) Disorders in central nervous system, such as epilepsy, mania, schizophrenia or ataxia; and
g) Diseases that arise from, or are aggravated by, insufficient blood flow through a particular organ or portion thereof, e.g. heart attacks or strokes, the microvascular disease of diabetes mellitus, atherosclerosis, cerebral apoplexy (e.g. cerebral infarction, cerebral ischemia, etc.), or events resulting in a less prolonged loss of blood flow (e.g. angina pectoris, transient ischemic attacks, bowel ischemia, kidney ischemia, intermittent claudication of skeletal muscle, migraine headaches, Raynaud's phenomenon), or the like;

and more particularly for treatment and prevention of periodontitis; chronic pain; various leukemias; various rheumatisms; and disorders in central nervous system among above diseases, the compound (I) or its pharmaceutically acceptable salts of this invention are useful.

An ADA inhibitor, such as the compound (I) or its pharmaceutically acceptable salt of this invention, is useful for protection against the progression of glomerulosclerosis by suppressing glomerular hypertension and hyperfiltration, and thus useful for treatment and/or prevention of glomerulosclerosis.

An ADA inhibitor, such as the compound (I) or its pharmaceutically acceptable salt of this invention, is useful for complementing the defect of an IL-2 inhibitor, such as FK506, cyclosporin, or the like, in immunosuppressive effects. Thus, the combination use of the two compounds enables treatment and prevention of various diseases and conditions in need of immunosuppression.

And additionally, a series of the compounds disclosed in our previous patents and patent applications of this field (e.g. WO00/05217, WO00/55155, WO01/53271), may be also useful for treatment and/or prevention of these diseases mentioned above.

Any patents, patent applications, and publications cited herein are incorporated by reference.

In order to illustrate the usefulness of the object compound (I), the pharmacological test data of the compound (I) are shown in the following.

Adenosine Deaminase (ADA) Enzyme Assay

Test Compound:
1-{(3R,4S)-4-Hydroxy-1-[2-(4-ethoxyphenyl)-4-benzoxazolyl]-3-pentyl}-imidazole-4-carboxamide hydrochloride (E0023)
1-{(3R,4S)-4-Hydroxy-1-[2-(2-thienyl)-7-benzoxazolyl]-3-pentyl}-imidazole-4-carboxamide hydrochloride (E0028)

Test Method:
The reaction velocity (V) is measured by a change in absorbance at 265 nm (A265) resulting from the deamination of adenosine. Human ADA was expressed and purified from ADA-deficient bacterial strain. Reaction mixtures of a total volume of 200 µl contained 0.16 µg/ml of ADA and 0.1 mM of adenosine and test compound in 10 mM phosphate buffer saline (pH 7.4). The reaction was started by addition of ADA to a mixture of adenosine and test compound. The reaction was followed at room temperature by recording decrease in A265 for 3 minutes in SPECTRAmax 250 (Molecular Devices, USA) to automatically calculate Vmax. Inhibitory potency of test compound was expressed as IC50 value, the drug concentration required to produce 50% inhibition of Vmax in comparison to vehicle treatment.

Results:

| Test Compound | IC50 (nM) |
| --- | --- |
| E0023 | <20 |
| E0028 | <20 |

BEST MODE FOR CARRYING OUT THE INVENTION

The following examples are provided to further illustrate details for the preparation of the compounds of the present invention. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Those skilled in the art will readily understand that known variations of the conditions and processes of the following preparative procedures can be used to prepare these compounds.

The starting materials and intermediates are prepared by the application or adaptation of known methods, for example methods as described in the Reference Examples or their obvious chemical equivalents.

The abbreviations, symbols and terms used in the Preparations, Examples and Formulae have the following meanings.

DMF N,N-dimethylformamide
EtOAc Ethyl acetate
THF Tetrahydrofuran
r.t. Room temperatures
L-Selectride® Lithium tri- sec-butylborohydride
Pd—C Palladium on carbon powder Preparation 1 p-Chlorobenzoyl chloride (5.17 ml) was added dropwise to a solution of 2-amino-3-methylphenol (5.0 g) and pyridine (3.93 ml) in N,N-dimethylformamide (DMF; 41 ml) at 5-10° C. The mixture was stirred overnight and poured into ice water. The precipitates were collected, washed with water, and dried to give a pale brown powder (8.3 g).

To this powder were added toluene (100 ml) and p-toluenesulfonic acid monohydrate (0.5 g). The mixture was heated overnight under Dean-Stark condition, washed with an aqueous NaOH solution, dried, and evaporated to afford a pale brown crystals of 2-(4-chlorophenyl)-4-methylbenzoxazole (P0001; 5.47 g).

Preparation 2

A mixture of 2-(4-chlorophenyl)-4-methylbenzoxazole (P0001; 5.44 g), N-bromosuccinimide (4.77 g) and 2,2'-azobisisobutyronitrile (92 mg) in $CCl_4$ (54 ml) was refluxed overnight. The insoluble was removed by filtration, and the filtrate was concentrated and cooled. The precipitates were collected and washed with $CCl_4$ to give pale brown crystals of 2-(4-chlorophenyl)-4-(bromomethyl)benzoxazole (P0002; 6.31 g).

Preparation 3

A mixture of 2-(4-chlorophenyl)-4-(bromomethy)benzoxazole (P0002; 2.0 g) and hexamethylenetetramine (1.27 g) in acetic acid (15 ml) and water (7.5 ml) was refluxed for 3 hours and evaporated. EtOAc and an aqueous $NaHCO_3$ solution were added, and the organic layer was separated, dried, and evaporated. The residue (1.47 g) was purified by silica gel (25 g) column chromatography eluting with hexane-$CH_2Cl_2$-EtOAc (5:1:1) to give pale yellow crystals of 2-(4-chlorophenyl)benzoxazole-4-carbaldehyde (P0003; 0.89 g).

Preparation 4 n-Butyl lithium/hexane (1.6M; 1.01 ml) was added dropwise below −50° C. under nitrogen to a solution of dimethyl [(S)-3-(tert-butyldimethylsilyloxy)butan-2-on-1-yl]phosphonate (0.50 g; Tetrahedron Lett., 1990, 31, 5733) in THF (3 ml). The mixture was stirred for 10 min. 2-(4-Chlorophenyl)benzoxazole-4-carbaldehyde (P0003; 415 mg) and THF (4 ml) were added. The reaction temperature was allowed to rise gradually to 0° C. and kept for 6 hr, then at r.t. for 1 day. Sat. $NaHCO_3$ (10 ml) and $CH_2Cl_2$ (10 ml) were added. The organic layer was washed with water, dried and evaporated to give an oil (0.74 g). Column chromatography on silica gel (22 g) eluting with hexane-EtOAc (30:1) gave a yellow oil of (S)-4-(tert-butyldimethylsilyloxy)-1-[2-(4-chlorophenyl)-4-benzoxazolyl]-1-penten-3-one (P0004; 0.51 g).

Preparation 5

L-Selectride®/THF (1.0M; 1.36 ml) was added below −40° C. under nitrogen to a solution of (S)-4-(tert-butyldimethylsilyloxy)-1-[2-(4-chlorophenyl)-4-benzoxazolyl]-1-penten-3-one (P0004; 0.50 g) in THF (7 ml). The mixture was stirred at −20° C. for 30 min. EtOAc and water were added. The organic layer was washed with brine, dried and evaporated to give an oil (0.62 g). Column chromatography on silica gel (20 g) eluting with hexane-EtOAc (20:1) gave a colorless oil of (3S,4S)-4-(tert-butyldimethylsilyloxy)-1-[2-(4-chlorophenyl)-4-benzoxazolyl]-1-penten-3-ol (P0005; 389 mg).

Preparation 6

A mixture of (3S,4S)-4-(tert-butyldimethylsilyloxy)-1-[2-(4-chlorophenyl)-4-benzoxazolyl]-1-penten-3-ol (P0005; 385 mg) and 10% Pd—C (77 mg) in EtOAc (19 ml) was stirred under hydrogen atmosphere at atmospheric pressure for 20 min. Pd—C was removed by filtration and the filtrate was evaporated to give a colorless oil of (3S,4S)-4-(tert-butyldimethylsilyloxy)-1-[2-(4-chlorophenyl)4-benzoxazolyl]pentan-3-ol (P0006; 0.40 g).

Preparation 7

Triethylamine (0.248 ml) was added to an ice-cooled solution of (3S,4S)-4-(tert-butyldimethylsilyloxy)-1-[2-(4-chlorophenyl)-4-benzoxazolyl]-pentan-3-ol (P0006; 0.40 g) and methanesulfonyl chloride (0.139 ml) in dichloromethane (13 ml) and the mixture was stirred at 5° C. for 30 min. The mixture was washed with water, dried and evaporated. The residual oil (494 mg) was chromatographed over silica gel (15 g) eluting with a mixture of hexane and dichloromethane (2:1) to dichloromethane to give a colorless oil of (3S,4S)4-(tert-butyldimethylsilyloxy)-1-[2-(4-chlorophenyl)-4-benzoxazolyl]-3-pentyl methanesulfonate (P0007; 372 mg).

Preparation 8

The following compound was prepared in a similarly to that of Preparation 1.

Methyl 2-(4-chlorophenyl)benzoxazole-7-carboxylate (P0008)

Preparation 9

Methyl 2-(4-chlorophenyl)benzoxazole-7-carboxylate (P0008; 1.79 g) and THF (15 ml) were added portionwise to an ice-cooled suspension of $LiAlH_4$ (236 mg) in diethyl ether (10 ml). The mixture was stirred overnight. 10% $H_2SO_4$ (2.76 ml) was added dropwise to the ice-cooled above mixture and the mixture was filtered through Celite. The filtrate was washed with brine, dried and evaporated to give a pale brown powder (1.63 g).

A mixture of this powder and $MnO_2$ (4.89 g) in $CHCl_3$ (40 ml) was refluxed for 7 hours. The insoluble was removed by filtration and washed with $CH_2Cl_2$. The filtrate was evaporated and the residue was chromatographed over silica gel (30 g) eluting with hexane-$CH_2Cl_2$ (5:1) to hexane-$CH_2Cl_2$-EtOAc (4:1:1) to give pale yellow crystals of 2-(4-chlorophenyl)benzoxazole-7-carbaldehyde (P0009; 1.21 g).

Preparation 10

The following compound was prepared similarly to Preparation 4.

(S)-4-(tert-Butyldimethylsilyloxy)-1-[2-(4-chlorophenyl)-7-benzoxazolyl]-1-penten-3-one (P0010)

Preparation 11

The following compound was prepared similarly to Preparation 5.

(3S,4S)-4-(tert-Butyldimethylsilyloxy)-1-[2-(4-chlorophenyl)-7-benzoxazolyl]-1-penten-3-ol (P0011)

Preparation 12

The following compound was prepared similarly to Preparation 6.

(3S,4S)-4-(tert-Butyldimethylsilyloxy)-1-[2-(4-chlorophenyl)-7-benzoxazolyl]-pentan-3-ol (P0012)

Preparation 13

The following compound was prepared similarly to Preparation 7.

(3S,4S)-4-(tert-Butyldimethylsilyloxy)-1-[2-(4-chlorophenyl)-7-benzoxazolyl]-3-pentyl methanesulfonate (P0013)

Preparation 14

To a stirred suspension of $Cs_2CO_3$ (1.05 g) and dimethyl [(S)-3-(tert-butyldimethylsilyloxy)butan-2-on-1-yl]phosphonate (1.0 g) in isopropyl alcohol (15 ml), 2-(benzyloxy)-3-nitrobenzaldehyde (870 mg) was added at 0° C. The resulting mixture was allowed to warm to r.t. and stirred for 3 hours.

After quenching with 5% aqueous citric acid solution, the product was extracted with ethyl acetate. The organic extract was washed with a 5% aqueous citric acid solution, water, and brine, and the organic layer was dried over sodium sulfate. Evaporation gave the product (1.59 g) as yellow syrup.

The residue was purified by silica gel (31 g) column chromatography eluting with hexane/ethyl acetate (10:1) to give (S)-1-(2-benzyloxy-3-nitrophenyl)-4-(tert-butyldimethylsilyloxy)-1-penten-3-one (P0014; 1.169 g) as pale-yellow oil.

Preparation 15

The following compound was prepared similarly to Preparation 5.

(3S,4S)-1-(2-benzyloxy-3-nitrophenyl)-4-(tert-butyldimethylsilyloxy)-1-penten-3-ol (P0015).

Preparation 16

A mixture of (3S,4S)-1-(2-benzyloxy-3-nitrophenyl)-4-(tert-butyldimethylsilyloxy)-1-penten-3-ol (P0015; 610 mg) and 10% Pd—C (120 mg) in EtOAc (6 ml) was stirred under hydrogen atmosphere at atmospheric pressure for 1 hour. Pd—C was removed by filtration through Celite. The filtrate was filtered through silica gel (6 g) and evaporated to give (3S,4S)-1-(3-amino-2-hydroxyphenyl)-4-(tert-butyldimethylsilyloxy)pentan-3-ol (P0016; 444.9 mg) as a brown solid.

Preparation 17

A mixture of (3S,4S)-1-(3-amino-2-hydroxyphenyl)-4-(tert-butyldimethylsilyloxy)pentan-3-ol (P0016; 445 mg) and 4-chlorobenzaldehyde (192 mg) in toluene (15 ml) was refluxed for 2 hours. And then to the resulting mixture of the Schiffs base was added manganese triacetate (733 mg) and the reaction mixture was refluxed for 1 hour. The precipitated manganese diacetate was then separated by filtration and the solvent was removed under reduced pressure. The crude product was purified by silica gel (26 g) column chromatography eluting with hexane/ethyl acetate (20:1) to give (3S,4S)-4-(tert-butyldimethylsilyloxy)-1-[2-(4-chlorophenyl)-7-benzoxazolyl]pentan-3-ol (P0012; 465 mg).

EXAMPLE 1

A suspension of imidazole-4-carboxamide (111 mg) in DMF (0.93 ml) was treated with NaH (60% in mineral oil; 45.5 mg), and the mixture was stirred at r.t. for 30 min. A solution of (3S,4S)-4-(tert-butyldimethylsilyloxy)-1-[2-(4-chlorophenyl)-4-benzoxazolyl]-3-pentyl methanesulfonate (P0001; 372 mg) in DMF (3.4 ml) was added and the resulting mixture was stirred at 85° C. for 5 days. The mixture was poured into water and extracted with EtOAc. The extract was washed with water, dried, and evaporated. Column chromatography on silica gel (10 g) eluting with $CH_2Cl_2$-methanol (40:1) gave a colorless oil of 1-{(3R,4S)4-(tert-butyldimethylsilyloxy)-1-[2-(4-chlorophenyl)-4-benzoxazolyl]-3-pentyl}imidazole-4-carboxamide (E0001; 0.16 g).

In the same manner as in Example 1, obtained were compounds of Example 2 to 16 shown in Table 1.

EXAMPLE 17

1M solution of tetrabutylammonium fluoride in THF (0.387 ml) was added to a solution of 1-{(3R,4S)-4-(tert-butyldimethylsilyloxy)-1-[2-(4-chlorophenyl)-4-benzoxazolyl]-3-pentyl}imidazole-4-carboxamide (E0001; 0.16 g) in THF (7 ml) and the mixture was stirred at r.t. for 2 hours. EtOAc and water were added and the organic layer was separated, washed with water, dried and evaporated. The residue (0.16 g) was chromatographed over silica gel (5 g) eluting with a mixture of dichloromethane and methanol (20:1 to 10:1). The desired product was treated with HCl in EtOAc to give a white powder of 1-{(3R,4S)-4-hydroxy-1-[2-(4-chlorophenyl)-4-benzoxazolyl]-3-pentyl}imidazole-4-carboxamide hydrochloride (E0017; 79.4 mg).

In the same manner as in Example 17, obtained were compounds of Example 18 to 32 shown in Table 2.

The physico-chemical data of the compounds of Preparations and Examples are shown in Table 3.

TABLE 1

| Example No. | Compound No. | Compound Name |
| --- | --- | --- |
| 2 | E0002 | 1-[(3R,4S)-4-(tert-Butyldimethylsilyloxy)-1-(2-phenyl-4-benzoxazolyl)-3-pentyl]imidazole-4-carboxamide |
| 3 | E0003 | 1-[(3R,4S)-4-(tert-Butyldimethylsilyloxy)-1-(2-phenyl-4-benzothiazolyl)-3-pentyl]imidazole-4-carboxamide |
| 4 | E0004 | 1-{(3R,4S)-4-(tert-Butyldimethylsilyloxy)-1-[2-(4-methoxyphenyl)-4-benzoxazolyl]-3-pentyl}imidazole-4-carboxamide |

TABLE 1-continued

| Example No. | Compound No. | Compound Name |
|---|---|---|
| 5 | E0005 | 1-{(3R,4S)-4-(tert-Butyldimethylsilyloxy)-1-[2-(3,4-dichlorophenyl)-4-benzoxazolyl]-3-pentyl}imidazole-4-carboxamide |
| 6 | E0006 | 1-{(3R,4S)-4-(tert-Butyldimethylsilyloxy)-1-[2-(4-fluorophenyl)-4-benzoxazolyl]-3-pentyl}imidazole-4-carboxamide |
| 7 | E0007 | 1-{(3R,4S)-4-(tert-Butyldimethylsilyloxy)-1-[2-(4-ethoxyphenyl)-4-benzoxazolyl]-3-pentyl}imidazole-4-carboxamide |
| 8 | E0008 | 1-{(3R,4S)-4-(tert-Butyldimethylsilyloxy)-1-[2-(4-chlorophenyl)-7-benzoxazolyl]-3-pentyl}imidazole-4-carboxamide |
| 9 | E0009 | 1-{(3R,4S)-4-(tert-Butyldimethylsilyloxy)-1-[2-(4-methoxyphenyl)-7-benzoxazolyl]-3-pentyl}imidazole-4-carboxamide |
| 10 | E0010 | 1-{(3R,4S)-4-(tert-Butyldimethylsilyloxy)-1-[2-(4-methylthiophenyl)-7-benzoxazolyl]-3-pentyl}imidazole-4-carboxamide |
| 11 | E0011 | 1-{(3R,4S)-4-(tert-Butyldimethylsilyloxy)-1-[2-(4-methylphenyl)-7-benzoxazolyl]-3-pentyl}imidazole-4-carboxamide |
| 12 | E0012 | 1-{(3R,4S)-4-(tert-Butyldimethylsilyloxy)-1-[2-(2-thienyl)-7-benzoxazolyl]-3-pentyl}imidazole-4-carboxamide |
| 13 | E0013 | 1-{(3R,4S)-4-(tert-Butyldimethylsilyloxy)-1-[2-(1-benzothien-2-yl)-7-benzoxazolyl]-3-pentyl}imidazole-4-carboxamide |
| 14 | E0014 | 1-{(3R,4S)-4-(tert-Butyldimethylsilyloxy)-1-[2-(3-chlorophenyl)-4-benzoxazolyl]-3-pentyl}imidazole-4-carboxamide |
| 15 | E0015 | 1-{(3R,4S)-4-(tert-Butyldimethylsilyloxy)-1-[2-(4-propoxyphenyl)-4-benzoxazolyl]-3-pentyl}imidazole-4-carboxamide |
| 16 | E0016 | 1-{(3R,4S)-4-(tert-Butyldimethylsilyloxy)-1-[2-(4-chlorophenyl)-5-benzoxazolyl]-3-pentyl}imidazole-4-carboxamide |

TABLE 2

| Example No. | Compound No. | Compound Name |
|---|---|---|
| 18 | E0018 | 1-[(3R,4S)-4-Hydroxy-1-(2-phenyl-4-benzoxazolyl)-3-pentyl]imidazole-4-carboxamide hydrochloride |
| 19 | E0019 | 1-[(3R,4S)-4-Hydroxy-1-(2-phenyl-4-benzothiazolyl)-3-pentyl]imidazole-4-carboxamide hydrochloride |
| 20 | E0020 | 1-{(3R,4S)-4-Hydroxy-1-[2-(4-methoxyphenyl)-4-benzoxazolyl]-3-pentyl}imidazole-4-carboxamide hydrochloride |
| 21 | E0021 | 1-{(3R,4S)-4-Hydroxy-1-[2-(3,4-dichlorophenyl)-4-benzoxazolyl]-3-pentyl}imidazole-4-carboxamide hydrochloride |
| 22 | E0022 | 1-{(3R,4S)-4-Hydroxy-1-[2-(4-fluorophenyl)-4-benzoxazolyl]-3-pentyl}imidazole-4-carboxamide hydrochloride |
| 23 | E0023 | 1-{(3R,4S)-4-Hydroxy-1-[2-(4-ethoxyphenyl)-4-benzoxazolyl]-3-pentyl}imidazole-4-carboxamide hydrochloride |
| 24 | E0024 | 1-{(3R,4S)-4-Hydroxy-1-[2-(4-chlorophenyl)-7-benzoxazolyl]-3-pentyl}imidazole-4-carboxamide |
| 25 | E0025 | 1-{(3R,4S)-4-Hydroxy-1-[2-(4-methoxyphenyl)-7-benzoxazolyl]-3-pentyl}imidazole-4-carboxamide hydrochloride |
| 26 | E0026 | 1-{(3R,4S)-4-Hydroxy-1-[2-(4-methylthiophenyl)-7-benzoxazolyl]-3-pentyl}imidazole-4-carboxamide |
| 27 | E0027 | 1-{(3R,4S)-4-Hydroxy-1-[2-(4-methylphenyl)-7-benzoxazolyl]-3-pentyl}imidazole-4-carboxamide |
| 28 | E0028 | 1-{(3R,4S)-4-Hydroxy-1-[2-(2-thienyl)-7-benzoxazolyl]-3-pentyl}imidazole-4-carboxamide hydrochloride |
| 29 | E0029 | 1-{(3R,4S)-4-Hydroxy-1-[2-(1-benzothien-2-yl)-7-benzoxazolyl]-3-pentyl}imidazole-4-carboxamide hydrochloride |
| 30 | E0030 | 1-{(3R,4S)-4-Hydroxy-1-[2-(3-chlorophenyl)-4-benzoxazolyl]-3-pentyl}imidazole-4-carboxamide hydrochloride |
| 31 | E0031 | 1-{(3R,4S)-4-Hydroxy-1-[2-(4-propoxyphenyl)-4-benzoxazolyl]-3-pentyl}imidazole-4-carboxamide hydrochloride |
| 32 | E0032 | 1-{(3R,4S)-4-Hydroxy-1-[2-(4-chlorophenyl)-5-benzoxazolyl]-3-pentyl}imidazole-4-carboxamide hydrochloride |

TABLE 3

| Compound No. | Physico-Chemical Data |
|---|---|
| P0001 | NMR(CDCl$_3$, δ): 2.67(3H, s), 7.10–7.60(5H, m), 8.20(2H, d, J=8Hz)<br>MS: 244(M+H)$^+$ |
| P0002 | NMR(CDCl$_3$, δ): 4.93(2H, s), 7.30–7.60(5H, m), 8.23(2H, d, J=8Hz) |
| P0003 | NMR(CDCl$_3$, δ): 7.40–7.60(3H, m), 7.80–8.00(2H, m), 8.28(2H, d, J=8Hz), 10.77(1H, s)<br>MS: 280(M+Na)$^+$ |
| P0004 | NMR(CDCl$_3$, δ): 0.12(3H, s), 0.14(3H, s), 0.97(9H, s), 1.44(3H, d, J=7Hz), 4.43(1H, q, J=7Hz), 7.30–7.70(5H, m), 7.90–8.30(4H, m)<br>MS: 464(M+Na)$^+$ |
| P0005 | NMR(CDCl$_3$, δ): 0.11(3H, s), 0.12(3H, s), 0.93(9H, s), 1.28(3H, d, J=6Hz), 2.74(1H, d, J=5Hz), 3.80–4.20(2H, m), 7.00–7.60(7H, m), 8.22(2H, d, J=8Hz)<br>MS: 466(M+Na)$^+$ |
| P0006 | NMR(CDCl$_3$, δ): 0.05(3H, s), 0.07(3H, s), 0.89(9H, s), 1.14(3H, d, J=6Hz), 1.80–2.00(2H, m), 3.00–3.40(4H, m), 3.70–3.80(1H, m), 7.10–7.60(5H, m), 8.19(2H, d, J=8Hz)<br>MS: 468(M+Na)$^+$ |
| P0007 | MS: 524(M+H)$^+$ |
| P0008 | NMR(CDCl$_3$, δ): 4.06(3H, s), 7.44(1H, t, J=8Hz), 7.54(2H, d, J=9Hz), 7.96(1H, dd, J=8.1Hz), 8.01(1H, dd, J=8.1Hz), 8.26(2H, d, J=9Hz)<br>MS: 310(M+Na)$^+$ |
| P0009 | NMR(CDCl$_3$, δ): 7.50–7.60(3H, m), 7.87(1H, dd, J=8.1Hz), 8.03(1H, dd, J=8.1Hz), 8.27(2H, d, J=8Hz), 10.43(1H, s) |
| P0010 | NMR(CDCl$_3$, δ): 0.12(3H, s), 0.15(3H, s), 0.95(9H, s), 1.43(3H, d, J=7Hz), 4.42(1H, q, J=7Hz), 7.30–7.60(4H, m), 7.70–8.00(3H, m), 8.24(2H, d, J=9Hz) |
| P0011 | NMR(CDCl$_3$, δ): 0.10(3H, s), 0.13(3H, s), 0.93(9H, s), 1.29(3H, d, J=6Hz), 2.77(1H, d, J=5Hz), 3.80–3.90(1H, m), 4.10–4.20(1H, m), 6.60–7.00(2H, m), 7.30–7.70(5H, m), 8.20(2H, d, J=8Hz)<br>MS: 466(M+Na)$^+$ |
| P0012 | NMR(CDCl$_3$, δ): 0.09(3H, s), 0.10(3H, s), 0.90(9H, s), 1.16(3H, d, J=6Hz), 1.80–2.00(2H, m), 2.46(1H, d, J=5Hz), 2.95–3.50(3H, m), 3.60–3.80(1H, m), 7.10–7.70(5H, m), 8.19(2H, d, J=8Hz)<br>MS: 468(M+Na)$^+$ |
| P0013 | MS: 546(M+Na)$^+$ |
| P0014 | NMR(CDCl$_3$, δ): 0.08(3H, s), 0.10(3H, s), 0.93(9H, s), 1.35(3H, d, J=7Hz), 4.33(1H, q, J=7Hz), 5.04(2H, s), 7.20–7.55(7H, m), 7.75–8.10(3H, m)<br>MS: 442(M+H)$^+$ |
| P0015 | NMR(CDCl$_3$, δ): 0.09(3H, s), 0.10(3H, s), 0.91(9H, s), 1.19(3H, d, J=6Hz), 2.68(1H, d, J=4Hz), 3.65–4.10(2H, m), 5.02(2H, s), 6.92(1H, dd, J=16.6Hz), 6.99(1H, d, J=16Hz), 7.10–7.55(6H, m), 7.71(2H, d, J=8Hz)<br>MS: 444(M+H)$^+$, 466(M+Na)$^+$ |
| P0016 | NMR(CDCl$_3$, δ): 0.08(3H, s), 0.09(3H, s), 0.90(9H, s), 1.08(3H, d, J=6Hz), 1.60–1.90(2H, m), 2.55–3.30(4H, m), 3.45–3.95(3H, m), 6.40–6.75(3H, m), 7.89(1H, brs) |
| E0001 | MS: 561(M+Na)$^+$ |
| E0002 | MS: 527(M+Na)$^+$ |
| E0003 | MS: 543(M+Na)$^+$ |
| E0004 | MS: 557(M+Na)$^+$ |
| E0005 | MS: 595(M+Na)$^+$ |
| E0006 | MS: 523(M+H)$^+$, 545(M+Na)$^+$ |
| E0007 | MS: 549(M+H)$^+$, 571(M+Na)$^+$ |
| E0008 | MS: 539(M+H)$^+$, 561(M+Na)$^+$ |
| E0009 | MS: 557(M+Na)$^+$ |
| E0010 | MS: 573(M+Na)$^+$ |
| E0011 | MS: 541(M+Na)$^+$ |
| E0012 | MS: 533(M+Na)$^+$ |
| E0013 | MS: 583(M+Na)$^+$ |
| E0014 | MS: 561(M+Na)$^+$ |
| E0015 | MS: 585(M+Na)$^+$ |
| E0016 | MS: 561(M+Na)$^+$ |
| E0017 | NMR(DMSO-d$_6$, δ): 0.97(3H, d, J=6Hz), 2.30–2.50(2H, m), 2.80–3.00(2H, m), 3.80–4.00(1H, m), 4.10–4.30(1H, m), 7.20–7.40(2H, m), 7.60–7.80(4H, m), 8.00–8.30(4H, m), 8.92(1H, s)<br>MS: 425(M+H)$^+$ |
| E0018 | NMR(CDCl$_3$, δ): 1.10(3H, d, J=6Hz), 2.20–3.20(4H, m), 3.90–4.20(2H, m), 5.42(1H, s), 6.90–7.30(3H, m), 7.40–7.60(5H, m), 7.78(1H, d, J=1Hz), 8.20–8.40(2H, m)<br>MS: 391(M+H)$^+$ |
| E0019 | NMR(CDCl$_3$, δ): 1.09(3H, d, J=6Hz), 2.30–2.60(3H, m), 2.90–3.30(2H, m), 3.90–4.10(2H, m), 5.39(1H, s), 6.99(1H, s), 7.10–7.40(2H, m), 7.40–7.80(6H, m), 8.00–8.20(2H, m)<br>MS: 407(M+H)$^+$ |
| E0020 | NMR(DMSO-d$_6$, δ): 0.98(3H, d, J=6Hz), 2.30–2.50(2H, m), 2.70–3.00(2H, m), 3.80–4.00(1H, m), 3.88(3H, s), 4.20–4.40(1H, m), 7.10–7.40(4H, |

TABLE 3-continued

| Compound No. | Physico-Chemical Data |
|---|---|
| | m), 7.58(1H, d, J=7Hz), 7.80(1H, s), 8.00–8.30(4H, m), 8.99(1H, s) MS: 421(M+H)⁺ |
| E0021 | NMR(CDCl₃, δ): 1.11(3H, d, J=6Hz), 2.31(1H, d, J=5Hz), 2.30–2.60(2H, m), 2.80–3.20(2H, m), 3.90–4.10(2H, m), 5.39(1H, s), 6.90–7.10(2H, m), 7.20–7.50(3H, m), 7.64(1H, d, J=8Hz), 7.78(1H, d, J=1Hz), 8.13(1H, dd, J=8.2Hz), 8.34(1H, d, J=2Hz) MS: 459(M+H)⁺ |
| E0022 | NMR(CDCl₃, δ): 1.10(3H, d, J=6Hz), 2.30–2.60(3H, m), 2.70–3.20(2H, m), 3.90–4.10(2H, m), 5.38(1H, s), 6.90–7.60(7H, m), 7.80(1H, d, J=1Hz), 8.20–8.40(2H, m) MS: 409(M+H)⁺ |
| E0023 | NMR(DMSO-d₆, δ): 0.99(3H, d, J=6Hz), 1.38(3H, t, J=7Hz), 2.30–2.50(2H, m), 2.70–3.00(2H, m), 3.80–4.00(1H, m), 4.10–4.30(3H, m), 7.10–7.40(4H, m), 7.58(1H, d, J=8Hz), 7.82(1H, s), 8.00–8.20(3H, m), 8.26(1H, s), 9.03(1H, s) MS: 435(M+H)⁺ |
| E0024 | NMR(DMSO-d₆, δ): 0.89(3H, d, J=6Hz), 2.20–2.50(2H, m), 2.60–2.80(2H, m), 3.80–3.90(1H, m), 3.90–4.10(1H, m), 5.10(1H, d, J=5Hz), 7.10–7.40(4H, m), 7.60–7.80(4H, m), 7.86(1H, s), 8.18(2H, d, J=8Hz) MS: 447(M+Na)⁺ |
| E0025 | NMR(DMSO-d₆, δ): 1.01(3H, d, J=6Hz), 2.30–2.50(2H, m), 2.70–3.00(2H, m), 3.80–4.00(1H, m), 3.89(3H, s), 4.20–4.40(1H, m), 7.10–7.40(4H, m), 7.58(1H, d, J=7Hz), 7.89(1H, s), 8.10(2H, d, J=9Hz), 8.22(1H, s), 8.35(1H, s), 9.15(1H, s) MS: 443(M+Na)⁺ |
| E0026 | NMR(CDCl₃, δ): 1.11(3H, d, J=6Hz), 2.00–2.10(1H, m), 2.20–2.60(2H, m), 2.56(3H, s), 2.70–3.00(2H, m), 3.90–4.10(2H, m), 5.43(1H, s), 6.90–7.10(2H, m), 7.20–7.60(5H, m), 7.78(1H, s), 8.12(2H, d, J=7Hz) MS: 459(M+Na)⁺ |
| E0027 | NMR(DMSO-d₆, δ): 0.89(3H, d, J=6Hz), 2.10–2.40(2H, m), 2.43(3H, s), 2.60–2.80(2H, m), 3.70–4.10(2H, m), 5.09(1H, d, J=5Hz), 7.00–7.40(4H, m), 7.45(2H, d, J=8Hz), 7.61(1H, d, J=7Hz), 7.76(1H, s), 7.83(1H, s), 8.08(2H, d, J=8Hz) MS: 427(M+Na)⁺ |
| E0028 | NMR(DMSO-d₆, δ): 0.98(3H, d, J=6Hz), 2.30–2.50(2H, m), 2.70–2.90(2H, m), 3.80–4.00(1H, m), 4.20–4.30(1H, m), 7.20–7.40(3H, m), 7.59(1H, d, J=8Hz), 7.72(1H, s), 7.90–8.10(3H, m), 8.24(1H, s), 8.89(1H, s) MS: 419(M+Na)⁺ |
| E0029 | NMR(DMSO-d₆, δ): 0.99(3H, d, J=6Hz), 2.20–2.60(2H, m), 2.70–3.00(2H, m), 3.80–4.00(1H, m), 4.20–4.40(1H, m), 7.20–7.40(2H, m), 7.40–7.80(4H, m), 8.00–8.30(5H, m), 8.89(1H, s) MS: 469(M+Na)⁺ |
| E0030 | NMR(DMSO-d₆, δ): 0.99(3H, d, J=6Hz), 2.30–2.50(2H, m), 2.80–3.00(2H, m), 3.80–4.00(1H, m), 4.20–4.30(1H, m), 7.20–7.50(2H, m), 7.60–7.90(4H, m), 8.10–8.20(3H, m), 8.24(1H, s), 9.04(1H, s) MS: 447(M+Na)⁺ |
| E0031 | NMR(DMSO-d₆, δ): 0.99(3H, d, J=6Hz), 1.01(3H, t, J=7Hz), 1.70–1.90(2H, m), 2.30–2.50(2H, m), 2.80–2.90(2H, m), 3.80–4.00(1H, m), 4.06(2H, t, J=7Hz), 4.20–4.40(1H, m), 7.10–7.40(4H, m), 7.58(1H, d, J=8Hz), 7.87(1H, s), 8.10(2H, d, J=9Hz), 8.22(1H, s), 8.31(1H, s), 9.11(1H, s) MS: 471(M+Na)⁺ |
| E0032 | NMR(DMSO-d₆, δ): 0.98(3H, d, J=6Hz), 2.20–2.40(2H, m), 2.50–2.70(2H, m), 3.80–4.00(1H, m), 4.10–4.30(1H, m), 7.20–7.30(1H, m), 7.60–7.80(5H, m), 8.00–8.30(4H, m), 8.97(1H, s) MS: 447(M+Na)⁺ |

The invention claimed is:

1. A compound of the formula (I):

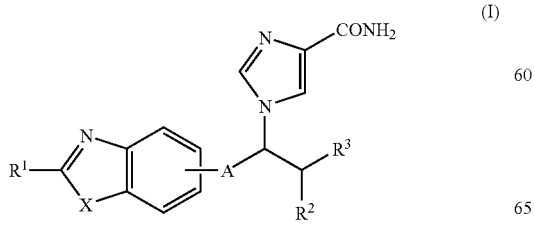

wherein R¹ is an optionally substituted phenyl, thienyl, or benzothienyl,
R² is lower alkyl;
R³ is hydroxy or protected hydroxy;
X is O or S; and
-A- is ethylene;
or a salt thereof.

2. The compound according to claim 1, wherein R¹ is thienyl.

3. The compound according to claim 1, wherein R¹ is an optionally substituted phenyl with substituent(s) selected from the group consisting of halogen, lower alkyl, lower alkoxy, lower alkylthio, lower alkylsulfinyl and lower alkylsulfonyl.

4. The compound according to claim 1, wherein A is ethylene and $R^2$ is methyl.

5. The compound according to claim 1, wherein the compound is selected from the group consisting of:
(1) 1-{(3R,4S)-4-hydroxy-1-[2-(4-chlorophenyl)-4-benzoxazolyl]-3-pentyl}-imidazole-4-carboxamide hydrochloride,
(2) 1-[(3R,4S)-4-Hydroxy-1-(2-phenyl-4-benzoxazolyl)-3-pentyl]-imidazole-4-carboxamide,
(3) 1-{(3R,4S)-4-Hydroxy-1-[2-(4-methoxyphenyl)-4-benzoxazolyl]-3-pentyl}-imidazole-4-carboxamide hydrochloride,
(4) 1-{(3R,4S)-4-Hydroxy-1-[2-(4-ethoxyphenyl)-4-benzoxazolyl]-3-pentyl}-imidazole-4-carboxamide hydrochloride;
(5) 1-{(3R,4S)-4-Hydroxy-1-[2-(4-chlorophenyl)-7-benzoxazolyl]-3-pentyl}-imidazole-4-carboxamide,
(6) 1-{(3R,4S)-4-Hydroxy-1-[2-(4-methoxyphenyl)-7-benzoxazolyl]-3-pentyl}imidazole-4-carboxamide hydrochloride,
(7) 1-{(3R,4S)-4-Hydroxy-1-[2-(4-methylthiophenyl)-7-benzoxazolyl]-3-pentyl}-imidazole-4-carboxamide,
(8) 1-{(3R,4S)-4-Hydroxy-1-[2-(4-methylphenyl)-7-benzoxazolyl]-3-pentyl}-imidazole-4-carboxamide,
(9) 1-{(3R,4S)-4-Hydroxy-1-[2-(2-thienyl)-7-benzoxazolyl]-3-pentyl}-imidazole-4-carboxamide hydrochloride,
(10) 1-{(3R,4S)-4-Hydroxy-1-[2-(2-benzothienyl)-7-benzoxazolyl]-3-pentyl}-imidazole-4-carboxamide hydrochloride,
(11) 1-{(3R,4S)-4-Hydroxy-1-[2-(3-chlorophenyl)-4-benzoxazolyl]-3-pentyl}-imidazole-4-carboxamide hydrochloride,
(12) 1-{(3R,4S)-4-Hydroxy-1-[2-(4-propoxyphenyl)-4-benzoxazolyl]-3-pentyl}-imidazole-4-carboxamide hydrochloride, and
(13) 1-{(3R,4S)-4-Hydroxy-1-[2-(4-chlorophenyl)-5-benzoxazolyl]-3-pentyl }-imidazole-4-carboxamide hydrochloride.

6. A pharmaceutical composition comprising the compound of claim 1 as an active ingredient and a pharmaceutically acceptable, substantially non-toxic carrier or excipient.

7. A process for producing the compound of claim 1, comprising any of the following steps (1) to (2):
(1) reacting a compound of formula (III):

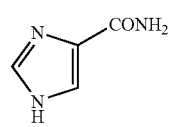

(III)

with a compound of formula (IV):

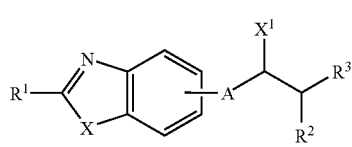

(IV)

wherein $R^1$, $R^2$, $R^3$, X and A are as defined above, and $X^1$ is hydroxy or a leaving group, provided that $R^3$ is not hydroxy; or (2) reacting a compound of formula (I-1):

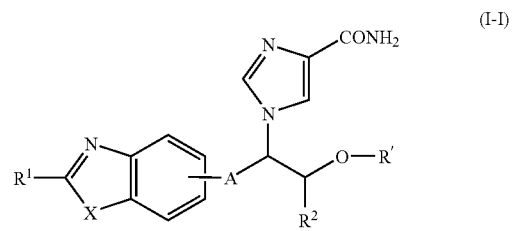

(I-1)

wherein $R^1$, $R^2$, X and A are as defined above, and $R'$ is hydroxy protective group, with a deprotecting agent.

8. The compound according to claim 2, wherein A is ethylene and $R^2$ is methyl.

9. A pharmaceutical composition comprising the compound of claim 5 as an active ingredient and a pharmaceutically acceptable, substantially non-toxic carrier or excipient.

10. The compound according to claim 3, wherein A is ethylene and $R^2$ is methyl.

11. The compound according to claim 1, wherein $R^1$ is benzothienyl.

12. The compound according to claim 11, wherein A is ethylene and $R^2$ is methyl.

13. The compound according to claim 1, wherein $R^1$ is phenyl.

14. The compound according to claim 13, wherein A is ethylene and $R^2$ is methyl.

15. The compound according to claim 5, wherein the compound is 1-{(3R,4S)-4-hydroxy-1-[2-(4-chlorophenyl)-4-benzoxazolyl]-3-pentyl}-imidazole-4-carboxamide hydrochloride.

16. The compound according to claim 5, wherein the compound is 1-[(3R,4S)-4-Hydroxy-1-(2-phenyl-4-benzoxazolyl)-3-pentyl]-imidazole-4-carboxamide.

17. The compound according to claim 5, wherein the compound is 1-{(3R,4S)-4-Hydroxy-1-[2-(4-methoxyphenyl)-4-benzoxazolyl]-3-pentyl}-imidazole-4-carboxamide hydrochloride.

18. The compound according to claim 5, wherein the compound is 1-{(3R,4S)-4-Hydroxy-1-[2-(4-ethoxyphenyl)-4-benzoxazolyl]-3-pentyl}-imidazole-4-carboxamide hydrochloride.

19. The compound according to claim 5, wherein the compound is 1-{(3R,4S)-4-Hydroxy-1-[2-(4-chlorophenyl)-7-benzoxazolyl]-3-pentyl}-imidazole-4-carboxamide.

20. The compound according to claim 5, wherein the compound is 1-{(3R,4S)-4-Hydroxy-1-[2-(4-methoxyphenyl)-7-benzoxazolyl]-3-pentyl}-imidazole-4-carboxamide hydrochloride.

21. The compound according to claim 5, wherein the compound is 1-{(3R,4S)-4-Hydroxy-1-[2-(4-methylthiophenyl)-7-benzoxazolyl]-3-pentyl}-imidazole-4-carboxamide.

22. The compound according to claim 5, wherein the compound is 1-{(3R,4S)-4-Hydroxy-1-[2-(4-methylphenyl)-7-benzoxazolyl]-3-pentyl}-imidazole-4-carboxamide.

23. The compound according to claim 5, wherein the compound is 1-{(3R,4S)-4-Hydroxy-1-[2-(2-thienyl)-7-benzoxazolyl]-3-pentyl}-imidazole-4-carboxamid hydrochloride.

24. The compound according to claim 5, wherein the compound is 1-{(3R,4S)-4-Hydroxy-1-[2-(2-benzothienyl)-7-benzoxazolyl]-3-pentyl}-imidazole-4-carboxamide hydrochloride.

25. The compound according to claim 5, wherein the compound is 1-{(3R,4S)-4-Hydroxy-1-[2-(3-chlorophenyl)-4-benzoxazolyl]-3-pentyl }-imidazole-4-carboxamide hydrochloride.

26. The compound according to claim 5, wherein the compound is 1-{(3R,4S)-4-Hydroxy-1-[2-(4-propoxyphenyl)-4-benzoxazolyl]-3-pentyl}-imidazole-4-carboxamide hydrochloride.

27. The compound according to claim 5, wherein the compound is 1-{(3R,4S)-4-Hydroxy-1-[2-(4-chlorophenyl)-5-benzoxazolyl]-3-pentyl }-imidazole-4-carboxamide hydrochloride.

* * * * *

UNITED STATES PATENT AND TRADEMARK OFFICE
CERTIFICATE OF CORRECTION

PATENT NO. : 7,317,107 B2
APPLICATION NO. : 10/503585
DATED : January 8, 2008
INVENTOR(S) : Kiyoshi Tsuji et al.

It is certified that error appears in the above-identified patent and that said Letters Patent is hereby corrected as shown below:

Column 3, line 43, "Alternatively, the compound (II) can be reacted"
should read -- Alternatively, the compound (III) can be reacted --.

Column 10, line 41, "The following compound was prepared in a similarly to"
should read -- The following compound was prepared similarly to --.

Column 21, line 3, "benzoxazolyl]-3-pentyl}-imidazole-4-carboxamid"
should read -- benzoxazolyl]-3-pentyl}-imidazole-4-carboxamide --.

Signed and Sealed this

Twenty-ninth Day of July, 2008

JON W. DUDAS
*Director of the United States Patent and Trademark Office*